United States Patent [19]

MacDonald

[11] Patent Number: 4,660,984
[45] Date of Patent: Apr. 28, 1987

[54] REFLECTOMETER FEATURING AN INTEGRATED CAVITY OF ENHANCED EFFICIENCY

[75] Inventor: Stuart G. MacDonald, Webster, N.Y.

[73] Assignee: Eastman Kodak Company, Rochester, N.Y.

[21] Appl. No.: 858,549

[22] Filed: Apr. 30, 1986

Related U.S. Application Data

[63] Continuation-in-part of Ser. No. 646,405, Sep. 4, 1984, abandoned.

[51] Int. Cl.$^4$ ............................................. G01N 21/47
[52] U.S. Cl. ................................... 356/446; 250/228; 356/236
[58] Field of Search .............................. 356/445–448, 356/236; 250/228

[56] References Cited

U.S. PATENT DOCUMENTS 4,022,534  5/1977  Kishner ........................... 356/236 X
4,076,421  2/1978  Kishner ........................... 356/446
4,277,177  7/1981  Larsen et al. ..................... 356/446

*Primary Examiner*—Vincent P. McGraw
*Attorney, Agent, or Firm*—Dana M. Schmidt

[57] ABSTRACT

There is disclosed a reflectometer which uses an integrating cavity interposed between a pulsed light source and a test element. The cavity has enhanced efficiency by reason of its construction wherein a diffusely-reflecting surface is connected at opposite edges to mirrored surfaces that reflect back to the diffusely-reflecting surface, at least the majority of diffusely-reflected rays that are non-aligned with selected rays from the diffusely-reflecting surface that impinge unimpeded on the test element.

11 Claims, 6 Drawing Figures

4,660,984

REFLECTOMETER FEATURING AN INTEGRATED CAVITY OF ENHANCED EFFICIENCY

This is a continuation-in-part of application Ser. No. 646,405, filed Sept. 4, 1984, now abandoned.

FIELD OF THE INVENTION

This invention relates to a reflectometer useful in detecting reflection densities $D_R$ in test elements, and more particularly, to one that uses a pulsed light source and an integrating means.

BACKGROUND OF THE INVENTION

Reflectometers have been constructed with a variety of light sources. Pulsed sources, such as a pulsed xenon source, have the following advantages: (a) high ratio of usable light to power and heat generated; and (b) a use of power that is limited to the time when a test element is to be read. A pulsed xenon source is particularly useful in illuminating at wavelengths between 300 and 400 nm, such wavelengths being of particular interest for certain test elements. However, such pulsed light sources have the disadvantage of being structured rather than diffuse. That is, the arc itself rather than a general light is imaged. The structure and position of the arc generating the light varies from pulse to pulse as does the color temperature. Therefore, it has been well recognized that reflectometers using such a source require integrating means to convert the structured light into diffuse light. Examples are shown in FIG. 1 of U.S. Pat. No. 4,076,421 and in U.S. Pat. No. 4,022,534 wherein a mirrored surface is used in conjunction with a diffusely transmitting surface. One problem with such prior reflectometers has been that light that is not initially diffusely sent direct to the sample, tends to be lost. For example, the device of the '421 patent states such light is either absorbed by the wells of the cavity or reflected out through the detecting aperture, without ever striking the sample (col. 2, lines 36–38). The device of the '534 patent directs such light to baffles that absorb the light. Such lost light drastically reduces the efficiency of the reflectometer, necessitating a more powerful light source to make up for the reduction in efficiency. Such increased power requirements in turn have made the use of pulsed light sources less attractive, prior to this invention.

SUMMARY OF THE INVENTION

I have constructed a reflectometer which integrates the light from a pulsed source with improved efficiency. That is, I have provided integrating means which redirect light diffusely reflected to points other than the intended target, back to the diffusely-reflecting surface for re-reflection to the target.

More specifically, there is provided a reflectometer comprising means for supporting a generally planar test element in a predetermined location, such means including a transparent member or aperture permitting illumination of such a test element, a pulsed light source, integrating means optically disposed between the source and the predetermined location, and detector means for detecting radiation diffusely reflected from a supported test element, the detector means having an axis of detection extending to the predetermined location. The reflectometer is improved in that the integrating means comprises a diffusely-reflecting surface positioned about the axis so that at least one ray of light reflected from a portion of said surface passes optically unimpeded to the approximate middle of the transparent member or aperture, thereby defining a path of aligned illumination for such surface portion. The integrating means further comprises mirrored surfaces connected to opposite edges of the diffusely-reflecting surface and configured to reflect back to the diffusely-reflecting surface, at least the majority of the non-aligned light that is diffusely reflected from that surface portion.

Thus, it is an advantageous feature of the invention that a reflectometer is provided with means for integrating the light from a light source at levels of increased efficiency, thus permitting the use of a pulsed source.

It is a related advantageous feature of the invention that such a reflectometer has a high degree of utilization of the light from a pulsed light source.

Other advantageous features will become apparent upon reference to the following Description of the Preferred Embodiments, when read in light of the attached drawings.

DESCRIPTION OF THE PREFERRED EMBODIMENTS

The subject invention is described in connection with a preferred reflectometer wherein the test element contacts the reflectometer, and with preferred test elements containing a liquid analyte. In addition, it is applicable to any reflectometer wherein an integrating cavity of the invention is used, regardless of the form of the test element or whether it is in contact with the reflectometer. The reflectometer of this invention is also useful in measuring reflectivity of objects which do not receive liquids, such as dyed cloth, paper, photographic coatings, and plastics.

Preferred test elements are constructed to receive a liquid containing analytes and to produce a change detectable by reflected light. Most preferred are multi-zoned elements having a plurality of reagents and/or functions that are divided among layered zones. Highly preferred are elements in which the zones are separate but contiguous layers, for example, a multi-layered test element as described in U.S. Pat. No. 3,992,158, issued on Nov. 16, 1976, or in U.S. Pat. No. 4,258,001, issued on Mar. 24, 1981. The test elements of said patents include an uppermost layer that functions to transport the liquid to be tested to the next adjacent layer or layers. Such uppermost layer optionally includes a reagent for the test, for example, one or more enzymes operative upon the analyte of choice. The next adjacent layer or layers preferably include a matrix and binder and remaining reagents for the assay. These remaining reagents include those necessary to produce a detectable signal in increasing or decreasing amounts, e.g., a change in reflection density in response to the reaction of the analyte. Most preferably, such layers are formed to provide an integral element, within a support frame apertured to receive a liquid drop on the uppermost layer, as described, for example, in U.S. Pat. No. 4,169,751, issued on Oct. 2, 1979. (The terms "upper", "lower" and similar directional terms are used herein with respect to orientations of parts during their actual use.)

Figure 1:
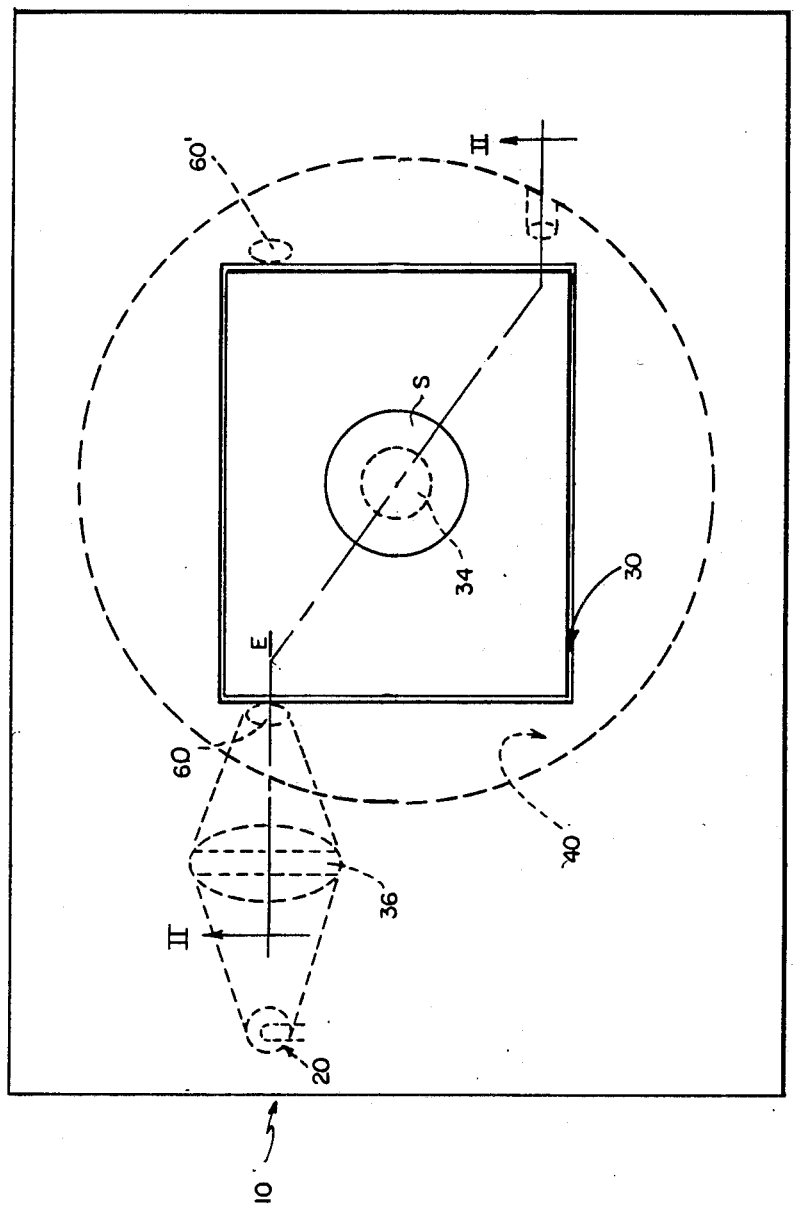
FIG. 1 is a plan view of a reflectometer of the invention.
Figure 2:
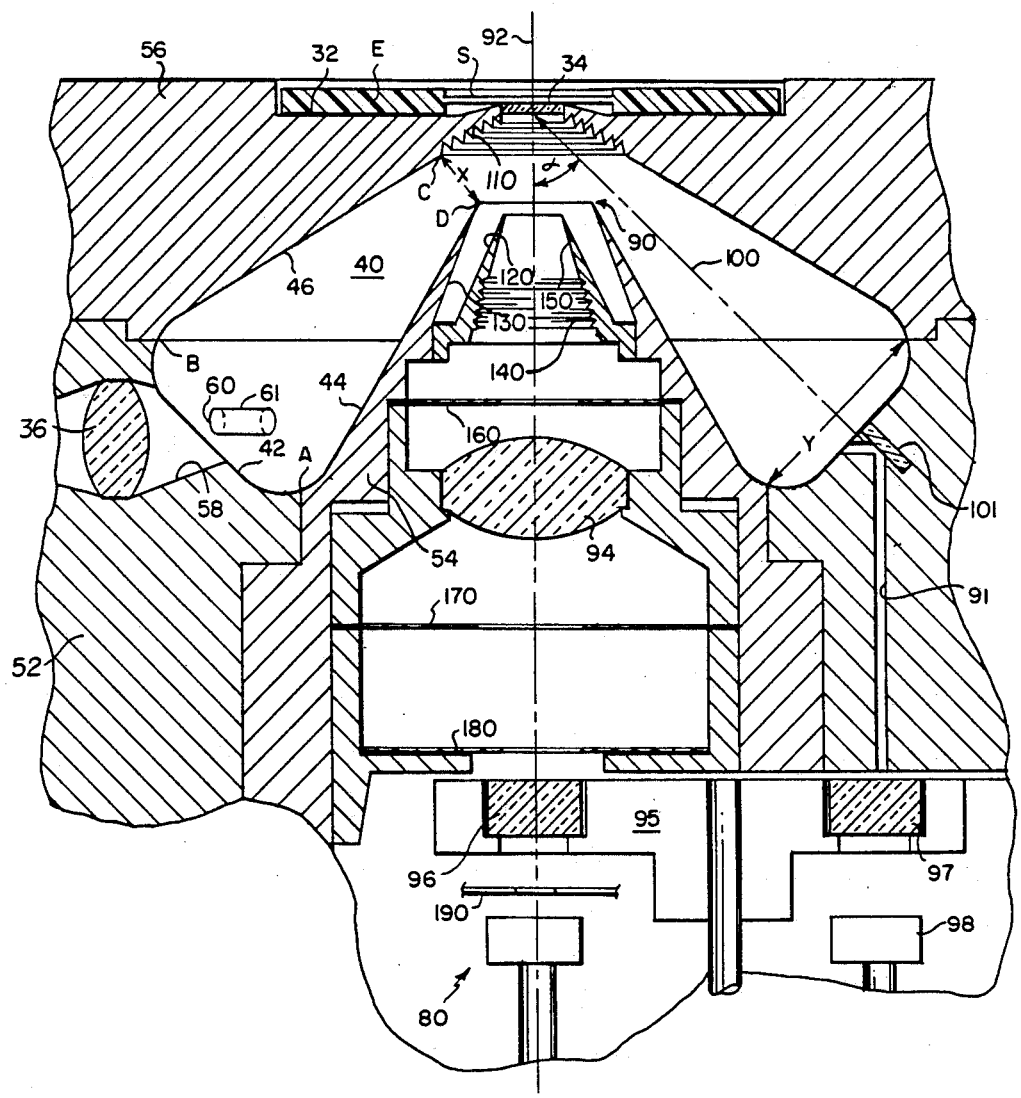
FIG. 2 is a fragmentary sectional view taken generally through the axis of the integrating cavity and along the line II—II of FIG. 1.

A reflectometer 10 constructed in accordance with the invention comprises, FIG. 1, a light source 20 which is preferably a pulsed source, a support surface 30 for a test element E to be read by the reflectometer, an integrating cavity 40 interposed between the light source and the support surface, and detector means 80, FIG. 2, for detecting diffusely-reflected signals from the test element. The detector means is mounted centered within a cone 90 having an axis 92, and receives light reflected from test element E through a conventional lens 94 and a filter wheel 95 having matched interference filters 96 and 97 appropriate to the wavelength to be detected. A conventional reference detector 98 receives light through filter 97 that is received via passageway 91 and mirror 101, directly from the integrating cavity 40. Detector means 80 and reference detector 98 are preferably matched photodiodes of the smallest surface area possible without vignetting the signal imaged upon them. Suitable examples include, e.g., the photodiodes obtainable from Hamamatsu Corp. under the model No. SD1227-66BQ. Such photodiodes are preferred because they have a very short path between cover window and active area, along the optical axis.

For careful control of the filter wheel for accurate repeated positioning of the filters, the wheel is rotated by a stepper motor, not shown, using encoder holes on the wheel to detect its position, as is conventional.

The pulsed source 20 can be selected from a variety of such sources, for example, a xenon arc lamp pulsed by a conventional charge storage circuit under the control of conventional computing means such as a microprocessor, not shown. Support surface 30 preferably comprises a recessed planar surface 32, FIG. 2, dimensioned to receive test element E, and a raised transparent viewing surface such as a sapphire member 34, raised to press against the viewable portion of test element E. Surface 32 is constructed to generally center the imaging portion of test element E on axis 92. Most preferably, such test element E is kept in position on surface 32 for the duration of its detection, since any displacement away from member 34 tends to distort the readings. The opposite, upper surface S of element E is the surface to which the analyte-containing liquid is added.

Member 34 can be omitted to leave just an aperture, although member 34 is preferred to keep dust and dirt from falling into cone 90.

A suitable conventional lens 36 is used to direct the light image from the pulsed source into cavity 40. An ellipsoidal reflector can also be used for higher energy efficiency.

In accord with one aspect of the invention, cavity 40 is constructed to ensure delivery of increased amount of diffuse radiation to test element E, originating from light source 20. To this end the cavity comprises a diffusely reflecting surface 42, extending from point A to point B in the cavity, FIG. 2, and mirrored surfaces 44 and 46 extending from respective points A and B to points C and D. For manufacturing convenience, the surfaces 42, 44 and 46 are shown as being the surfaces of separately manufactured blocks 52, 54 and 56, respectively, that join together at points A and B. A reflective passageway 58 is formed in block 52 to mount lens 36 and to direct incoming radiation through an aperture 60 into the cavity via an opening in surface 42. Passageway 58 preferably is aimed, using a shroud 61, at a spot 60', FIG. 1, on diffusely-reflecting surface 42, away from reflecting surface 44. That is, passageway 58 is not on an extension of a radius of the cone 90 as otherwise aperture 60 would be imaged on specularly-reflecting surface 44. The shroud is included to prevent light reflected from passageway 58 from reaching a surface 44 or 46. Such a preferred construction insures that diffuse light, rather than a specularly-reflected direct image of the light source, is directed to the test element.

Surface 42 is positioned to extend about axis 92. Preferably, it is a surface of revolution, and most preferably, a truncated conic surface of revolution having an axis that is coincident with axis 92. Although surface 42 is shown as being generally flat (in axial cross-section) except at corners A and B which are rounded, it can also be generated by revolving a curve about axis 92. Regardless of the shape of surface 42, at least one ray of light reflected from every portion of surface 42 passes without striking any reflective or absorbing surface (hereinafter, passes "unimpeded") through the approximate middle of member 34 and to test element E. If member 34 is omitted, it passes through the approximate middle of the aperture. Such a ray defines the path of intended aligned illumination, shown in FIG. 2 as a dot-dash arrow 100, for its portion of surface 42. If flat, except for corners A and B, as shown, surface 42 is preferably inclined so that the path of aligned illumination is traced by light reflected from the surface along a normal to strike the plane of member 34 at 45°. The inclination of surface 42, when viewed in axial cross-section as shown, is also preferably at a 45° angle to the plane of support surface 32. However, such angle of surface 42 to the plane of surface 32 can vary from about 30° to about 60°. Thus it is not essential that the normal rays from surface 42 proceed unimpeded to the test element. If such normal rays are the unimpeded rays, then there is approximately an equal distribution of non-aligned rays, as hereinafter defined, onto both the specularly-reflecting surfaces 44 and 46, providing best efficiencies. However, unequal distributions are also useful.

Regardless of the value of the angle that surface 42 makes with the plane of member 34, however, surface 42 is preferably shaped so that the rays along the path of aligned illumination form a cone of revolution. As noted, the intersection of the test element E by arrow 100 is at a preferred angle alpha of about 45°. However, angle alpha can vary between the angular limits imposed by surfaces 44 and 46, which is preferably between about 30° and about 60°.

As shown, surfaces 44 and 46 converge on the approximate center of member 34. However, this is not critical. Alternatively, these surfaces can converge on the side edges, respectively, of member 34 so as to allow more of the diffusely-reflected rays to reach the test element unimpeded.

Surface 42 is rendered diffusely reflective by any suitable technique, such as by the application of a flat white paint or a coating of pigments such as a coating of $BaSO_3$ or $TiO_2$ obtainable from Eastman Kodak under the brand name "Eastman White $TiO_2$".

Figure 3:
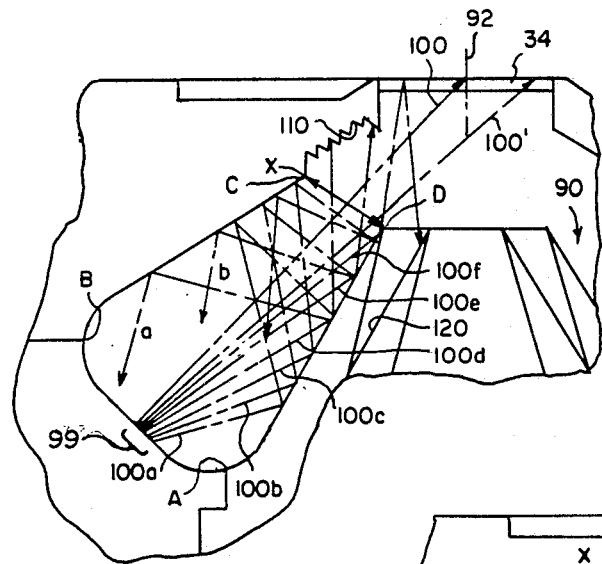
FIG. 3 is a fragmentary sectional view similar to that of FIG. 2 except that only the left-half portion of the cavity is detailed, to illustrate typical ray traces for one-half of the cavity, demonstrating the increased efficiency of the reflectometer.

Because surface 42 is diffusely reflective, light is reflected therefrom in all directions, FIG. 3, and not just in the direction of arrow 100. To return back to surface 42 at least the majority of the light that does not pass through member 34 to strike the test element, mirrored surfaces 44 and 46 are included, preferably contiguous with surface 42 at corners A and B. As used herein, "majority" means at least 50%. Any conventional specularly-reflecting surface, e.g., a mirror, suffices for such surfaces. As is readily apparent, surfaces 44 and 46 also comprise surfaces of revolution, and most preferably, conic surfaces.

An important aspect of cavity 40 is the configuration of surfaces 44 and 46 so that they reflect back to surface 42 the majority of non-aligned rays, that is, those reflected off surface 42 at an angle that deviates by more than about 5° from the intended path of aligned illumination. A configuration which is preferred for this effect is one in which surfaces 44 and 46 are convergent, that is, are closer together in the vicinity of the test element support provided by member 34, i.e., at points C and D, FIG. 2, than they are in the vicinity of surface 42, i.e., at points A and B. Thus, the distance "X", FIG. 2, is less than the distance "Y" (the distance from point A to point B).

As shown in FIGS. 2 and 3, surfaces 44 and 46 are surfaces of revolution generated by a straight line (except at the edges identified by points A and B).

Most preferably, surfaces 42, 44 and 46 are complete surfaces of revolution extending 360° around axis 92. In addition, the integrating cavity can be constructed so that such surfaces extend less than 360°, e.g., 355°.

Some ray traces emanating from one left-hand portion 99 of surface 42 of the aforedescribed embodiment are shown in FIG. 3. (The right-hand portion of the cavity, not shown, can be considered to be identical.) Trace 100 is normal to surface 42. Both traces 100 and 100' extend uninterrupted to member 34 and thus to test element E, wherein ray 100' is less than 5° from the corresponding normal ray 100. Rays 100a and 100b, which deviate by more than 5° from ray 100, bounce off surfaces 44, 46, 44 and 46, in that order, before returning to diffusely-reflecting surface 42. Ray 100c is reflected off surface 44 one additional time before it too returns.

Similarly, non-aligned rays emanating from other portions of surface 42 removed from center 99, are also reflected back. Most such other non-aligned rays also deviate about 5° from the corresponding aligned path before they strike a reflective surface 44 or 46. Thus it is clear that the convergence of surfaces 44 and 46 is effective to return to the diffusely-reflecting surface, most of the non-aligned rays, that is, those that deviate by more than about 5° from the corresponding unimpeded ray.

Similar ray traces can be drawn for other portions of surface 42.

The amount of convergence that occurs between the two mirrored surfaces 44 and 46 towards the support of the test element is not critical, except that a trade-off does occur in the needed power versus the redirection of non-aligned rays that occurs. That is, as convergence increases, the more will non-aligned rays be immediately returned to diffuse surface 42 for re-reflection as an aligned ray. However, increased convergence requires a larger diffuse area for surface 42 for a given value of aperture opening "X" onto the test element. As surface 42 increases in its linear separation dimension between the mirrored surfaces, the power lost in delivered brightness decreases approximately with the square of the linear increase.

As noted, surfaces 44 and 46 are shown as being inclined to the plane of member 34 at an angle of about 60° and about 30°, respectively. These angles are not critical, and in fact a greater convergence of surfaces 44 and 46 than is provided by this difference angle of about 30° tends to provide a more rapid return of non-aligned rays to surface 42, as already noted. However, if surface 44 is any steeper, i.e., is closer to 90°, less room is left for the light trap in cone 90 that is described hereinafter. If the difference between the angles for surfaces 44 and 46 is much more than about 30°, then the surface area for surface 42 is increased, with the concomitant decrease in power noted above.

It will be noted that special treatment is preferred for non-aligned rays 100d, 100e, and 100f. The reason is that rays 100d and 100e reflect off portions of the cavity, e.g., point D, that are so close to support member 34 that they could otherwise reflect into the detecting means 80 located at the bottom of cone 90, FIG. 2, without first encountering the test element. Ray 100f is objectionable because it provides undesired specular reflection from the test element (not shown) back into cone 90. For that reason, light traps are provided at surfaces 110, 120 and 130. Such trap surfaces can be ridged, as is preferred for surface 110, or smooth, such as is preferred for surfaces 120 and 130. Most preferably they are painted with a flat black paint. Thus, rays 100d, e and f are terminated by the traps. However, such rays constitute a very small percentage of the rays emanating from surface 42, and specifically, fall within a cone angle of only about 5°. This is a percentage of less than 5% of the 180° of possible diffuse reflection off surface 42, the remaining % of which proceeds directly to the test element as aligned rays, or is reflected back, as described, to surface 42 for re-emission. Thus, the reflectometer of the invention provides a recovery of the non-aligned rays that is on the order of 90%.

An additional light trap surface 140, FIG. 2, is provided on the inside surface 150 of cone 90 leading to lens 94. Additional light baffles 160, 170 and 180 are optionally included to insure the elimination of light specularly reflected from the bottom surfaces of member 34 and test element E. Also an aperture 190 preferably is included to define the viewed area on the test element.

Because of the increased efficiency described above, effective reflection density results have been achieved using the described pulsed light source and a conventional microprocessor, not shown, to make needed, conventional calculations. The instant invention provides increased energy efficiency while maintaining tight sample-to-reference channel balance and good signal-to-noise ratios across a range of reflection density $D_R$ values that includes 1.5 and across wavelengths as low as 340 nm.

Figure 4:
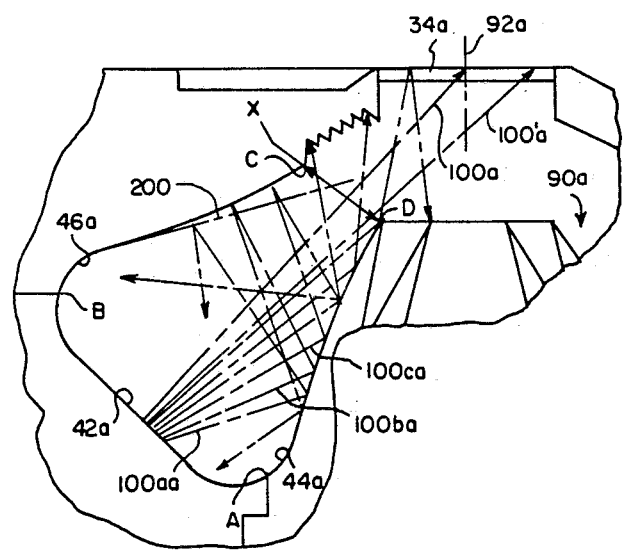
FIGS. 4 and 5 are sectional views similar to that of FIG. 3, except that alternate embodiments are illustrated.
Figure 5:
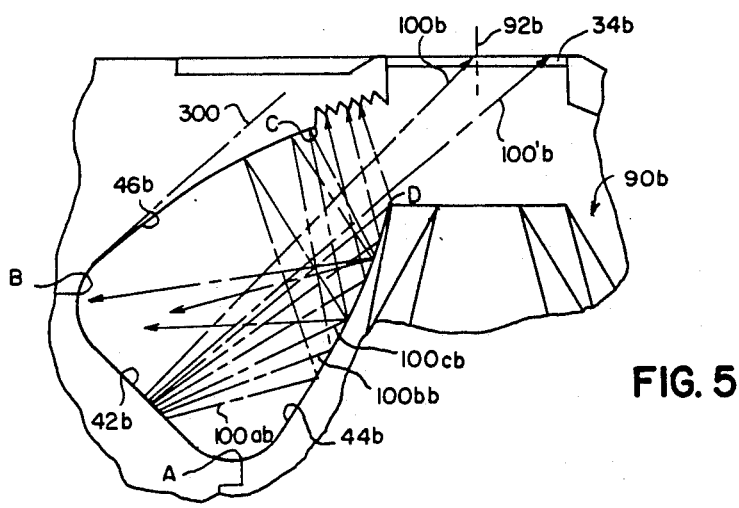

Although one preferred shape of surfaces 44 and 46 which permits X to be less than Y is the one in which surfaces 44 and 46 are generated by a straight line, as shown in FIGS. 2 and 3, other embodiments are also useful. Examples are shown in FIGS. 4 and 5. Parts similar to those previously described bear the same reference numeral, to which the distinguishing suffixes "a" and "b" are affixed.

In FIG. 4, the integrating means comprise a diffusely-reflecting surface 42a as before, the normals to which (100a) form intended paths of illumination that proceed unimpeded to member 34a and thus to a test element thereupon, not shown. Light diffusely reflected from such element is detected via a detector, as in the previous embodiment, located centered on axis 92a inside cone 90a. Rays within 5° of ray 100a, such as ray 100'a, also proceed unimpeded to the test element.

Unlike the previous embodiment, surfaces 44a and 46a, although still surfaces of revolution centered on axis 92a, are each generated by a revolved line that is curved all the way from point A or B to point D or C, respectively. In this embodiment, such generating line is convexly curved, that is, generates a surface that diverges more from the opposite mirrored surface than would have been the case for a surface-generating line that was straight (dot-dashed line 200 in FIG. 4). Such a surface has the advantage of more immediate reflection of non-aligned rays back to surface 42a. That is, rays 100aa and 100ba strike each of surfaces 44a and 46a only once before returning, and ray 100ca is reflected a total of 3 times only before returning. In each of these cases, this is two reflections less than was needed in the embodiment of FIG. 3. A disadvantage is that a larger surface 42a is needed, for the same value of X between C and D, which is less desirable for the power reasons noted above.

Similarly, in FIG. 5, the integrating means comprise a diffusely-reflecting surface 42b as before, the normals to which (100b) form intended paths of illumination that proceed unimpeded to member 34b and thus to a test element thereupon. Light diffusely reflected from such element is detected via a detector as in the previous embodiment. Rays within 5° of ray 100b, such as ray 100'b, also proceed unimpeded to the test element.

Unlike the previous embodiments, surfaces 44b and 46b, which are surfaces of revolution centered on axis 92b, are each generated by the revolution of a concavely curved line extending between B and C, and A and D, respectively. That is, the generating line converges more towards the opposite mirrored surface than would have been the case for a surface-generating line that was straight (line 300 in FIG. 5). Such a surface has the same advantage as the mirrored surfaces of FIG. 4—each non-aligned ray is specularly reflected two fewer times than the straight-line version of FIG. 3. See, e.g., the paths traced by rays 100ab, 100bb, and 100cb. However, cone 90b forms a sharper peak at edges D than was necessary in the previous embodiments, and is thus more difficult to manufacture.

It is not necessary that the generating line for the surfaces of revolution that provide the specular reflectance, e.g., surfaces 44 and 46, be a smooth curve. Other curve shapes are also useful, including lines with corners, provided that the distance X is less than the distance Y.

Figure 6:
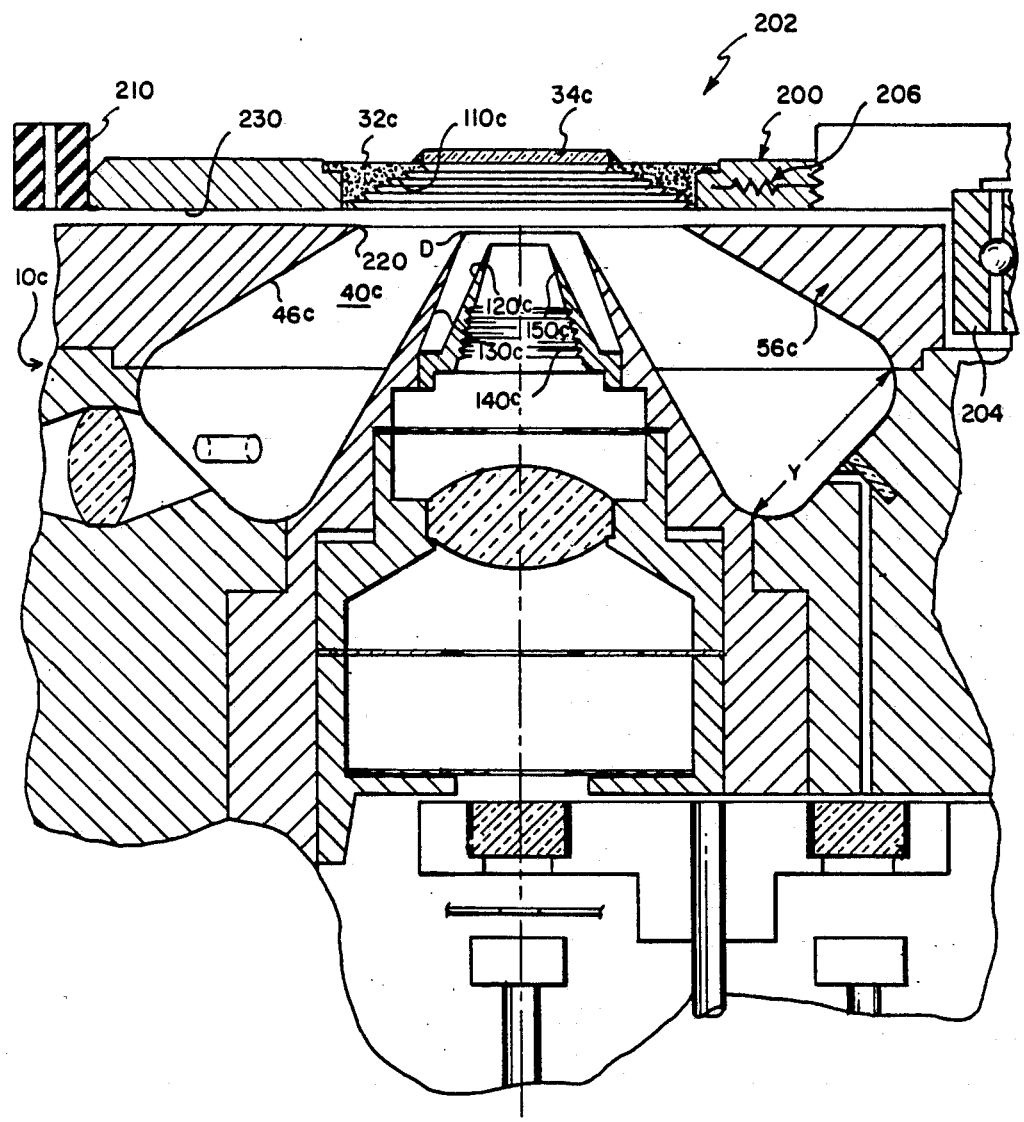
FIG. 6 is a sectional view similar to that of FIG. 2, except yet another alternate embodiment is illustrated.

More than one test element can be tested at a time using the reflectometer of this invention. In the embodiment shown in FIG. 6, the reflectometer 10c has the features of any one of the previously described embodiments, except that the test element supporting means and its associated light trap are not stationary with respect to the rest of the reflectometer. Parts similar to those previously described bear the same reference numeral, to which the distinguishing suffix "c" has been appended. Thus, planar support surface 32c is one of several positions 202 provided on a rotatable incubator disc 200 mounted on bearing 204. Such disc is provided with heating element 206 either within the disc, as shown, or otherwise associated therewith, such as within part 56c. Any drive means can be provided for the disc, for example a capstan drive using a drive roller 210. A raised transparent and thermally conductive window 34c is provided at each position 202, as described for previous embodiments. The cavity 40c and the associated light raps, including trap 110c, are constructed as described above, except that trap 110c extends out horizontally at least past the edge 220 of surface 46c.

To keep dust and dirt from falling into cavity 40c, an air stream can be jetted between the top of the reflectometer and undersurface 230 of disc 200.

To decrease the sensitivity of the optics to vertical displacement of disc 200, telecentric optics, not shown, are optionally used in a manner well known to the art.

In operation, disc 200 is rotated incrementally or continuously, by means such as roller 210, so that, one after the other, positions 202 are moved into place to be read by the optical system already described. The xenon arc lamp has a duration short enough that lateral movement of the test element during reading is essentially zero. Accurate time of the flash is achieved by individual trigger flags associated with each position on the disc; hence precise rotational control is not required.

The invention has been described in detail with particular reference to preferred embodiments thereof, but it will be understood that variations and modifications can be effected within the spirit and scope of the invention.

What is claimed is:

1. In a reflectometer comprising
    means for supporting a generally planar test element in a predetermined location, said means including a transparent member or aperture permitting illumination of such a test element,
    a light source,
    integrating means optically disposed between said source and said predetermined location,
    and detector means for detecting radiation diffusely reflected from a test element supported in said location, said detector means having an axis of detection extending to said predetermined location;
    the improvement wherein said integrating means comprises
    a diffusely reflecting surface positioned about said axis so that at least one ray of light reflected from a portion of said surface passes optically unimpeded to the approximate middle of said transparent member or aperture, thereby defining a path of aligned illumination for said surface portion,
    and mirrored surfaces connected to opposite edges of said diffusely-reflecting surface and configured to reflect back to said diffusely-reflecting surface, at least the majority of the non-aligned light that is diffusely reflected from said surface portion,
    whereby the efficiency of said reflectometer is increased.

2. A reflectometer as defined in claim 1, wherein said mirrored surfaces are configured to reflect back at least 90% of said non-aligned light.

3. A reflectometer as defined in claim 1, wherein said mirrored surfaces are the inside and the outside surfaces of two truncated cones centered on said axis, and said diffusely-reflecting surface is a surface of revolution generally centered on said axis.

4. A reflectometer as defined in claim 3, wherein said cone surfaces are sloped so that they are closer together in the vicinity of said test element support location than they are in the vicinity of said diffusely-reflecting surface, whereby said non-aligned light is redirected back to said diffusely-reflecting surface.

5. A reflectometer as defined in claim 1, wherein said diffusely-reflecting surface is a truncated conic surface and said unimpeded rays therefrom intersect a test element supported in said predetermined location at an angle that is between about 30° and about 60° to said supported test element.

6. A reflectometer as defined in claim 1, wherein said rays along said intended path of illumination form a cone.

7. A reflectometer as defined in claim 1, wherein said mirrored surfaces are surfaces of revolution generated by a substantially straight line, so that said mirrored surfaces are substantially flat when viewed in axial cross-section.

8. A reflectometer as defined in claim 1, wherein said mirrored surfaces are surfaces of revolution generated by a convexly curved line.

9. A reflectometer as defined in claim 1, wherein said mirrored surfaces are surfaces of revolution generated by a concavely curved line.

10. A reflectometer as defined in claim 1, and further including means for incubating more than one test element at a time in the vicinity of said detector means, and means for moving said incubating test elements sequentially into position for illumination by said light source.

11. A reflectometer as defined in claim 10, wherein said supporting means comprise a rotatable disc provided with multiple positions for holding such more than one test element, said moving means comprises means for rotating said disc either incrementally or continuously, and wherein said incubating means comprise at least one heating element associated with said disc.

* * * * *